United States Patent [19]

Bronson et al.

[11] 4,327,720
[45] May 4, 1982

[54] ESOPHAGEAL-ENDOTRACHEAL AIRWAY

[76] Inventors: Paul A. Bronson, Rte. 1, Box 239W; Patrick A. Wallace, 6810 Prutzman, Apt. #31, both of Beaumont, Tex. 77706

[21] Appl. No.: 5,645

[22] Filed: Jan. 22, 1979

[51] Int. Cl.³ .............................................. A61M 25/00
[52] U.S. Cl. ............................ 128/207.15; 128/349 B; 128/911
[58] Field of Search ............ 128/351, 349 B, 349 BV, 128/350 R, 145.5, 145.8, 208, 276, 207.14, 207.15

[56] References Cited

U.S. PATENT DOCUMENTS

| | | | |
|---|---|---|---|
| 3,322,126 | 5/1967 | Rusch et al. | 128/351 |
| 3,788,326 | 1/1974 | Jacobs | 128/207.15 |
| 3,905,361 | 9/1975 | Hewson et al. | 128/351 X |
| 4,090,518 | 5/1978 | Elam | 128/349 B |
| 4,231,365 | 11/1980 | Scarberry | 128/207.15 |

FOREIGN PATENT DOCUMENTS

| | | | |
|---|---|---|---|
| 68597 | 8/1969 | German Democratic Rep. | 128/207.15 |
| 429033 | 7/1967 | Switzerland | 128/349 B |
| 708477 | 5/1954 | United Kingdom | 128/349 B |

Primary Examiner—Henry J. Recla
Attorney, Agent, or Firm—Michael P. Breston

[57] ABSTRACT

The improved esophageal-endotracheal airway comprises an elongated flexible assembly having a shorter outer tube and a longer inner tube. The assembly is adapted to be inserted into the trachea or the esophagus. An expandable member is carried on the outer wall and near the distal end of each tube. The outer wall of the inner tube and the inner wall of the outer tube form an annular channel therebetween.

4 Claims, 13 Drawing Figures

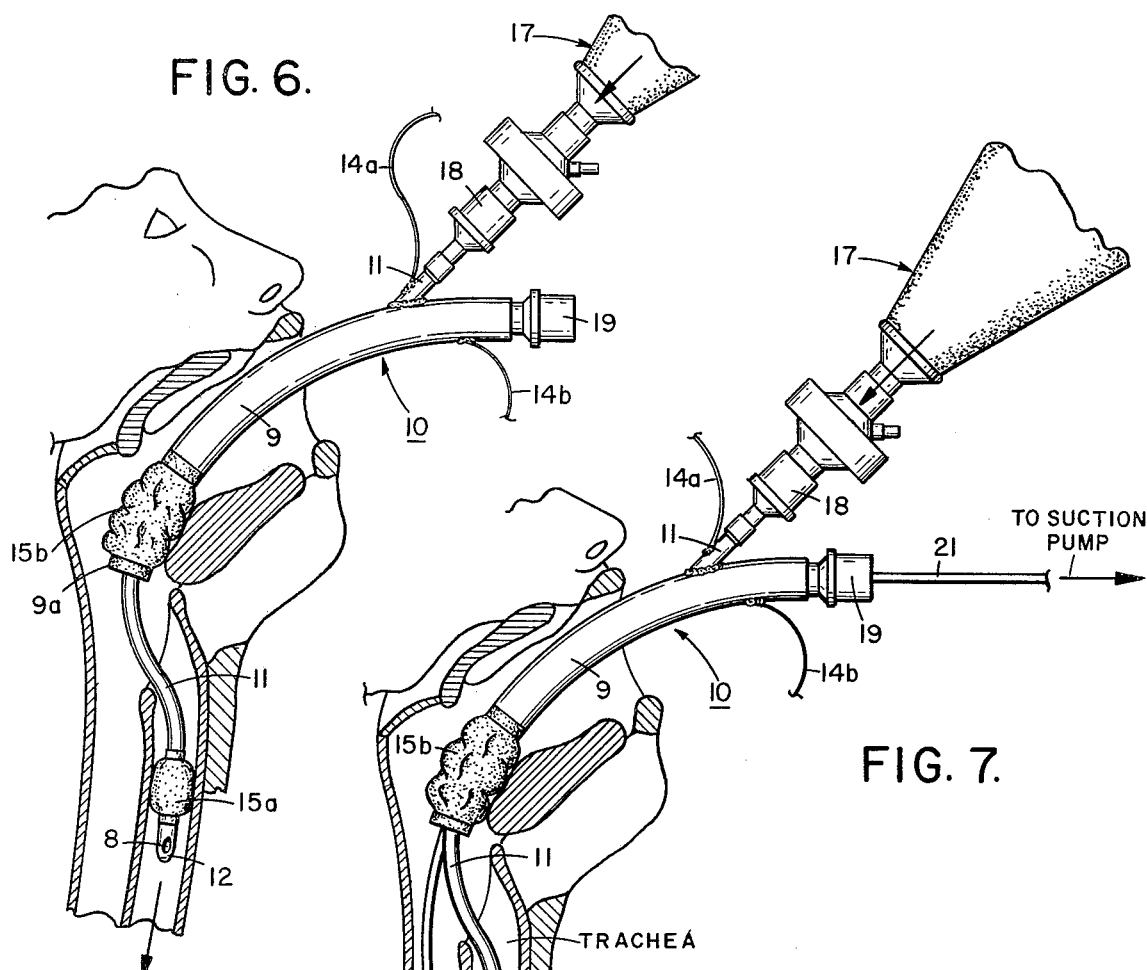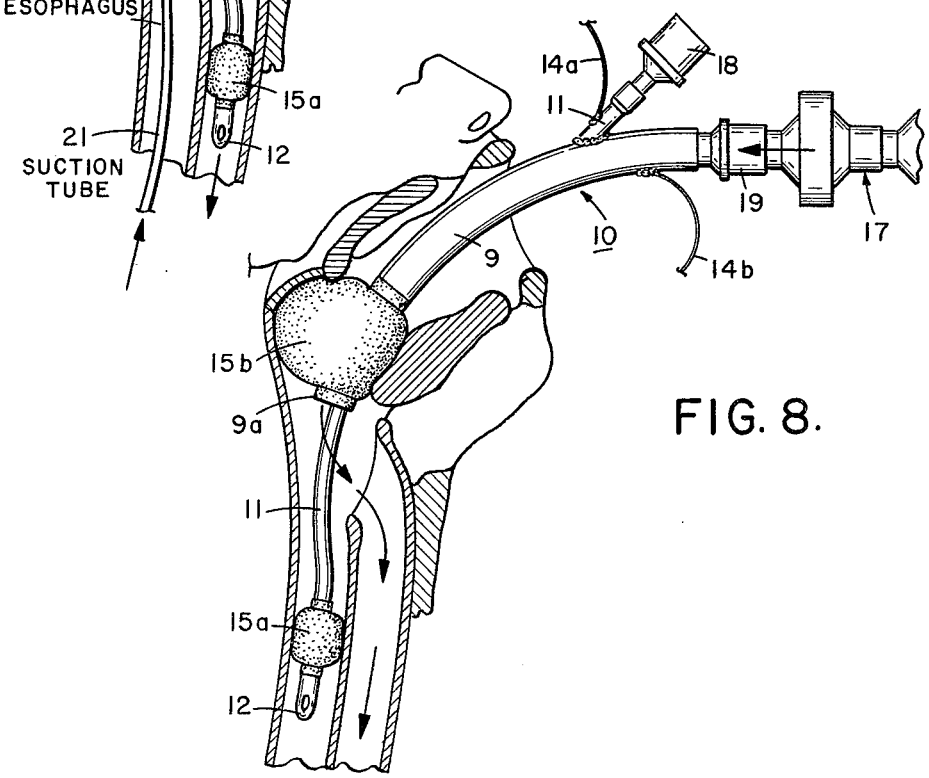

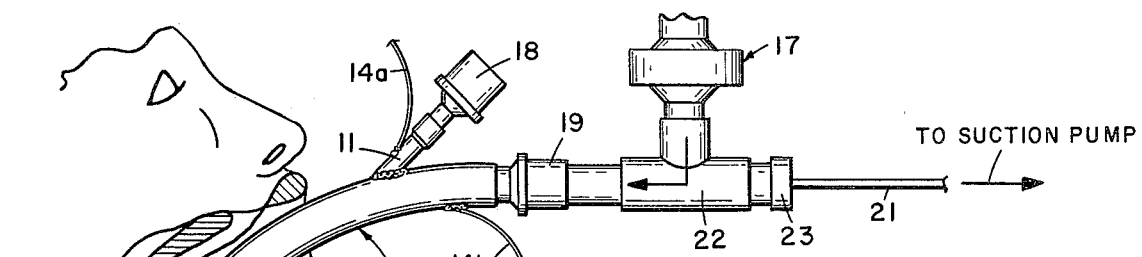
FIG. 9.
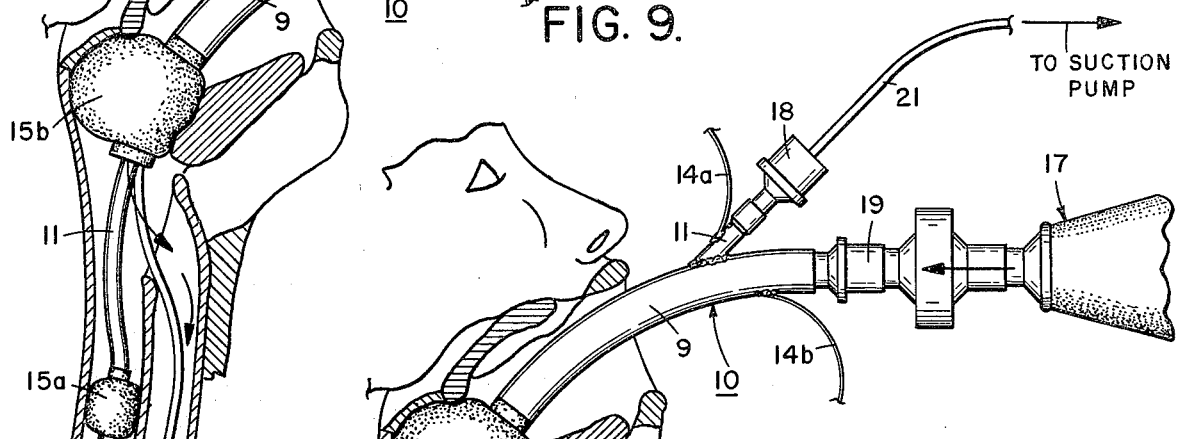
FIG. 10.
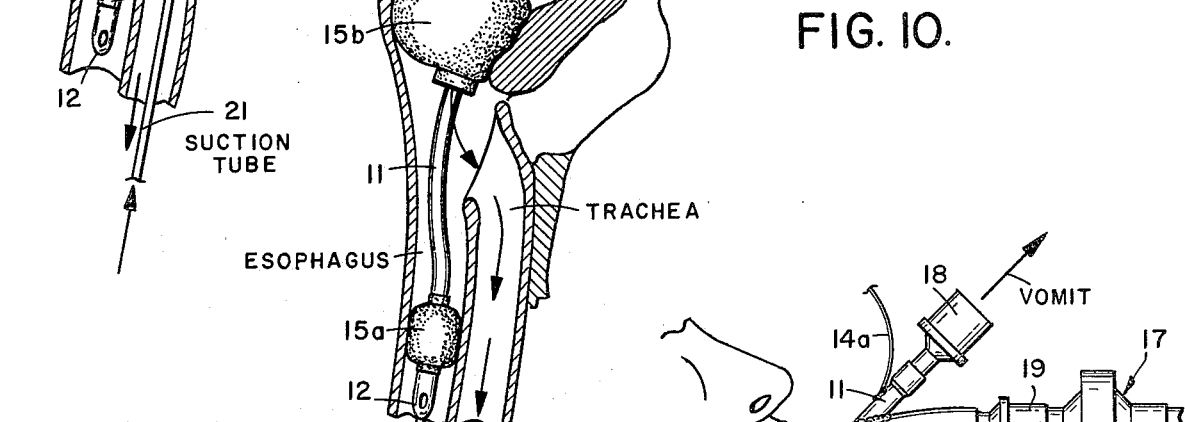
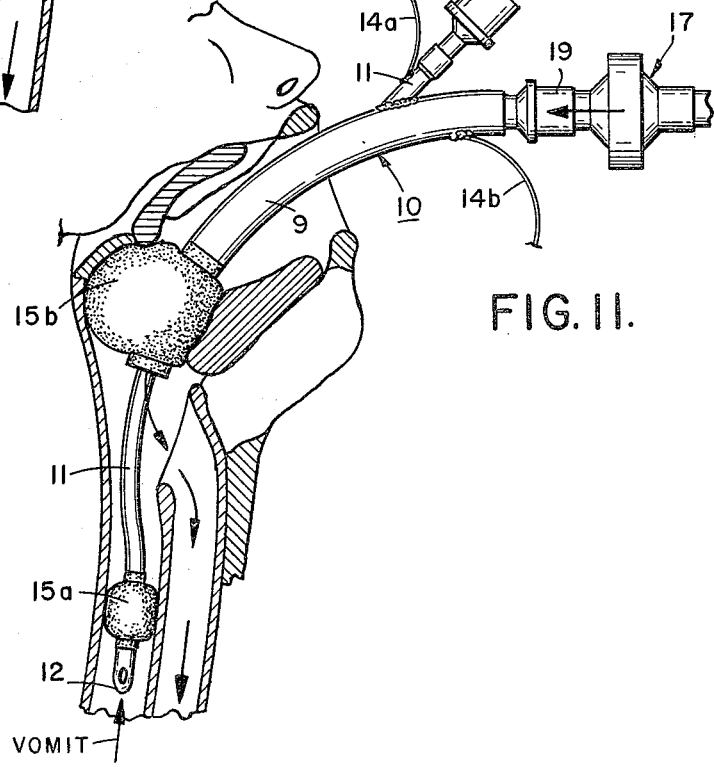
FIG. 11.

ESOPHAGEAL-ENDOTRACHEAL AIRWAY

REFERENCE TO RELATED APPLICATION

This application is related to copending application Ser. No. 907,066 filed on May 18, 1978, and now abandoned.

BACKGROUND OF THE INVENTION

An early airway apparatus for assisting in artificial respiration comprised an arcuate, open-ended tubular member which was adapted to be inserted into the trachea. The tubular member carried an external, inflatable resilient sleeve near the distal end thereof for effecting a seal with the inner wall of the trachea. The use of this early airway for moving air through the trachea into and out of the respiratory orifices required trained personnel, and therefore, was limited primarily to emergency rooms in hospitals.

In U.S. Pat. Nos. 3,683,908 and 3,841,319 is described another airway whose tubular member has a closed distal end. A plurality of openings are provided in the wall of the tubular member between the distal end and the proximal or mouthpiece end thereof. The tubular member is shaped to be inserted into the esophagus leading to the stomach rather than through the trachea leading to the lungs. An inflatable sleeve is carried by the tubular member near the distal end thereof for making a seal with the esophagus. Forced air passes from the tubular member through the openings and into the lungs of the respiratory system. To prevent the forced air from venting externally through the nose and mouth, there is provided a mask which is intended to seal the nose and mouth and to force the pumped air into the channels of the respiratory system.

But, if the close-ended tubular member were to be accidentally inserted into the trachea, as it may occasionally happen, the pumped air would move into the stomach instead of the lungs which may result in the death of the patient. This results from the airway having a closed end and the expandable sleeve sealing off the trachea.

Since no artificial respiration can take place, instead of filling the lungs with air, the tubular member would inflate the stomach, resulting in the expansion thereof followed by vomiting. When the administrator of the artificial respiration becomes aware of the accidental insertion of the tubular member into the trachea, he may attempt to deflate the sleeve, remove the tubular member from the trachea, and insert it into the esophagus. In the meantime, even if the operation is successful, the contents of the stomach could enter into the lungs.

The preceding problem is vaguely made reference to in said U.S. Pat. No. 3,683,908 (Col. 4, lines 32-35) which suggests making the outer diameter of the tubular member "of oral external-section." If this were to be done, presumably the diameter of the tubular member would be sufficiently large so as to prevent it from becoming inserted into the trachea. But a tube having such an oral external-section might damage the esophagus into which it is to be inserted.

In addition to the above described problem occurring when the tubular member is misguided into the trachea, there is another problem concerning the required mask which does not always provide an effective seal with the face because the face dimensions vary from patient to patient.

Another problem can be encountered when such a tubular member is inserted into the esophagus. During the process of resuscitation vomiting can occur. With vomiting high pressures are exerted from the stomach up through the esophagus. When the tubular member is in the esophagus with the sleeve inflated such that the vomit could not exit, excessive pressure becomes exerted at the junction zone between the stomach and esophagus. This pressure can be so high as to tear the esophagus away from the stomach with resulting hemorrhage.

In our copending patent application Ser. No. 907,066 is described an airway which overcomes the above described problems. The airway of this invention constitutes a substantial improvement and is simpler in construction and use, as will become apparent from the following description.

SUMMARY OF THE INVENTION

The improved airway for use in resuscitation comprises an elongated inner tube which can be inserted into the trachea or the esophagus. The inner tube is inside a shorter outer tube. The tubes form a passageway therebetween. An expandable member such as an inflatable sleeve is carried on the outer wall near the distal end of each tubular member. When the sleeves are expanded they form effective seals with the wall of the body channel. The inner tube extends through the wall of the outer tube near the proximal end thereof. The proximal end of each tube is adapted for being coupled to an air pump. Suction tubes can be inserted through the inner tube or through the passageway for pumping out either the stomach or the lungs.

BRIEF DESCRIPTION OF THE DRAWINGS

FIG. 6 shows the airway of the present invention whose inner tubular member becomes accidentally lodged in the trachea;

FIG. 7 shows the airway of the present invention with the inner tubular member in the trachea administering artificial resuscitation while simultaneously providing suction for the patient's stomach;

FIG. 8 shows the airway of the present invention in its normal use for administering artificial resuscitation with the inner tubular member in the esophagus and both sleeves inflated;

FIG. 9 is similar to FIG. 8 and in addition shows suction of the patient's lung;

FIG. 10 is similar to FIG. 8 and in addition shows suction of the stomach while artificial resuscitation continues;

FIG. 11 is similar to FIG. 8 except that vomit is expelled to atmosphere with no build up of pressure;

DETAILED DESCRIPTION OF THE PREFERRED EMBODIMENTS

Figure 2:
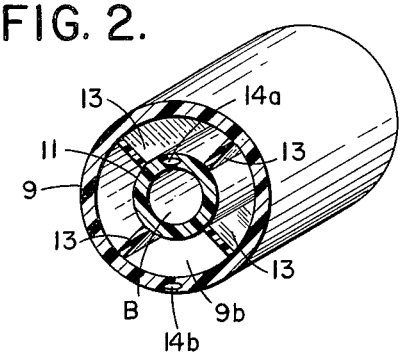
FIG. 2 is a transverse sectional view on line 2—2 of FIG. 1.

Throughout the drawings the same reference characters will be used to designate the same or similar parts to facilitate the understanding thereof.

Figure 1:
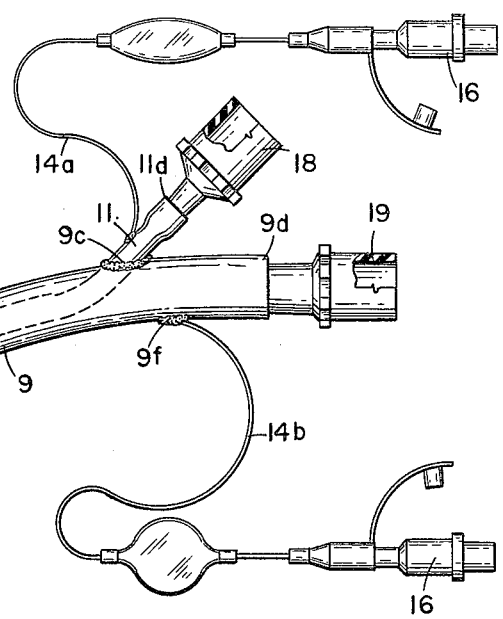
FIG. 1 is a perspective view of the present invention.
Figure 3:
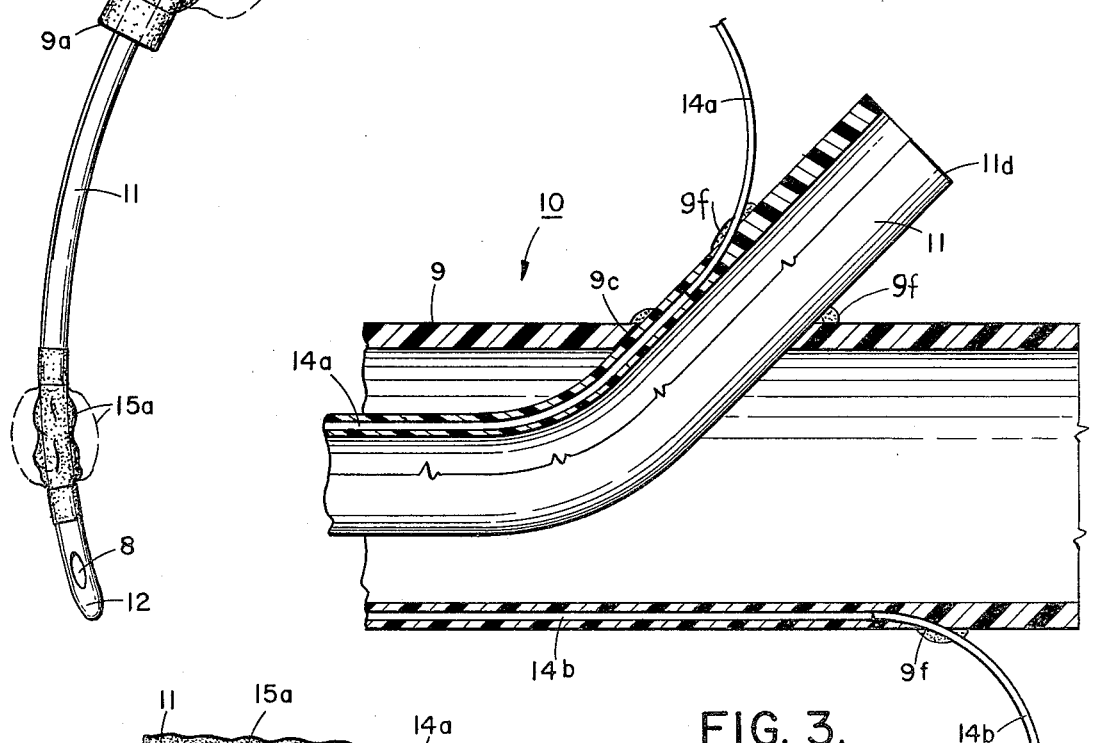
FIG. 3 is an enlarged longitudinal, sectional view of a portion of the airway near the junction of the tubular members.
Figure 4:
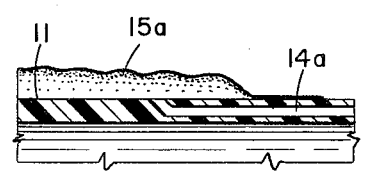
FIGS. 4-5 are fragmentary sectional views showing the air passageways to the sleeves on the inner and outer tubular members respectively.
Figure 5:
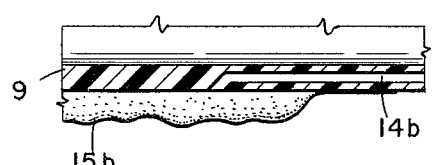
Figure 12:
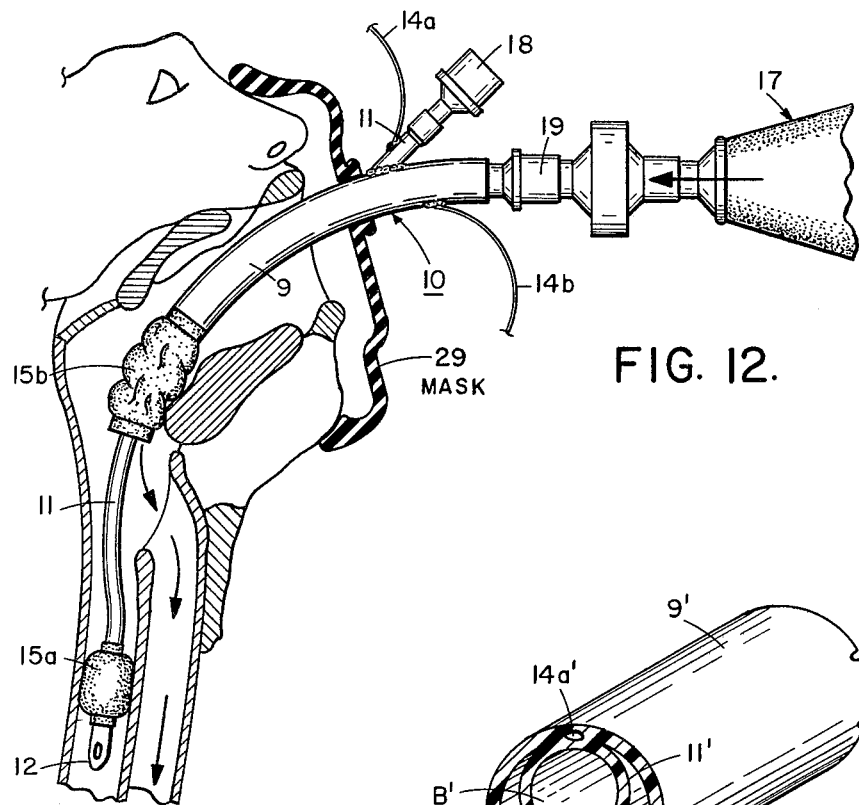
FIG. 12 is similar to FIG. 8 except that the proximal sleeve is deflated and a mask is used instead.

FIGS. 1-5 show the improved esophageal-endotracheal airway of the present invention, generally designated as 10, which includes an inner elongated flexible tubular member 11 having a bore B whose distal end 12 (FIG. 1) is open. An outer shorter flexible tubular member 9 can be concentrically mounted with the inner tube 11 (FIG. 2), and such concentricity is maintained by ribs 13, as shown. The distal end 9a of tube 9 is also open. The tubes define an annular passageway 9b therebetween. An expandable member, such as an inflatable sleeve 15a (FIG. 6), is mounted externally of the inner tubular member 11 near its distal end 12. Another inflatable sleeve 15b is mounted near the distal end 9a on tube 9. Air-carrying lines 14a and 14b admit pressurized air for inflating sleeves 15a and 15b, respectively. Each of lines 14a, 14b is coupled to a check valve 16 (FIG. 1). When the sleeves expand, as represented by the dotted lines, they form effective seals with the wall of the body channel, thereby closing off the airways leading from the nose and the mouth without requiring a facial mask. The inner tube 11 extends through an opening 9c (FIG. 3) in the wall of the outer tube 9 near the proximal end 9d thereof. The tubes 9 and 11 form a fluid-tight joint 9f therebetween. The proximal ends 9d and 11d of the tubes 9 and 11 are coupled to adapters 19 and 18, respectively. Each adapter can be coupled to a conventional air-operated pump 17 (FIGS. 6-12). The inner tube 11 is spaced from outer tube 9 by radial ribs 13 (FIG. 2). The tube 11 has a hole 8 therethrough, in a direction perpendicular to the longitudinal axis, to make its distal end 12 more flexible.

The use of the airway 10 will be illustrated in FIGS. 6-12. When the inner tubular member 11 becomes by accident inserted into the trachea (FIG. 6), the operator need only inflate sleeve 15a. Artificial resuscitation with pump 17 is produced through bore B (FIG. 2) of tubular member 11.

FIG. 7 illustrates that while artificial resuscitation is administered to the patient, the contents of the stomach can be emptied by inserting into the esophagus, through the annular passageway 9b, a suction tube 21 suitably coupled to a suction pump (not shown).

FIG. 8 shows the normal position of the airway 10 for administering artificial resuscitation. The tubular member 11 is inserted into the esophagus. Both sleeves 15a, 15b are inflated. Air is pumped by pump 17 into the tubular member 9. The air exits from the distal end 9a into the trachea leading to the patient's respiratory system.

FIG. 9 is similar to FIG. 8 except that a suction tube 21 is now inserted through a T-coupling member 22 into the tubular member 9 from which it exits into the trachea of the patient. The T-coupling has a packing gland 23. In this manner, artificial resuscitation can still take place while the contents of the respiratory system can be suctioned out.

As an immediate advantage of the invention, even when the tubular member 11 becomes by accident inserted into the trachea (FIG. 6), the artificial respiratory function can still be carried out, and in addition, the contents of the lungs and the contents of the stomach (FIG. 7) can be suctioned out. Also, during normal use of the airway (FIG. 8), artificial respiration can be maintained, while the contents of the lungs (FIG. 9) or the contents of the stomach (FIG. 10) are being sucked out.

FIG. 11 is similar to FIG. 8 except that regurgitation has taken place with vomit spilling out of tubular member 11 creating no contamination of the posterior pharynx and no build up in pressure at the junction of the stomach and esophagus.

Also, instead of the sleeve 15b being inflated as in FIG. 8, a mask 29 (FIG. 12) can be employed. No excessive pressure becomes developed at the union of the stomach and esophagus during vomiting since the bore B (FIG. 2) of tubular member 11 remains open to atmosphere while tube 11 is being inserted into the esophagus. Also, because sleeve 15a when inflated creates a seal against the esophagel wall no vomitis can contaminate the posterior pharynx.

Figure 13:
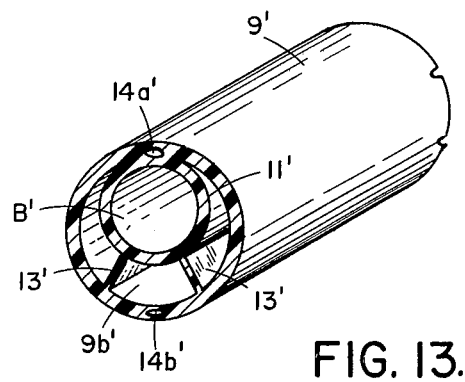
FIG. 13 is similar to FIG. 2 showing that the tubes need not be concentric.

In FIG. 13 is shown a modification wherein the same numerals followed by a prime (') are used to designate the same or similar parts. It will be noted that tubes 9 and 11 need not be concentric. In fact, the tubes can have their walls in touching relation as shown.

Other advantages of the invention will readily become apparent from the above description and modifications are possible. Such advantages and modifications are intended to be covered by the claims attached hereto.

What is claimed is:

1. An esophageal-endotracheal, flexible, tubular airway device adapted for insertion through the mouth, in normal use, into the esophagus and, in abnormal use, into the trachea of a patient, said device being adapted to provide separate passages for administering artificial respiration both when said device is lodged in the esophagus or in the trachea, said device comprising:

(a) a larger-diameter, shorter flexible tube having an open-ended proximal end portion and an open-ended distal end portion;

(b) a smaller-diameter, longer flexible tube having an open-ended proximal end portion and an open-ended distal end portion, said longer tube being disposed inside said shorter tube whereby the outer wall of said longer tube and the inner wall of said shorter tube define therebetween an annular fluid passageway wherein a suction tube could be extended through said passageway into said trachea or said esophagus for evacuating fluid contents therefrom while administering artificial respiration to the lungs, said annular passageway having an open outlet port at the distal end portion of said shorter tube, and said longer tube having a sufficient length adapted, in use, to reach into the esophagus below the mouth of the trachea, and said port of said annular passageway to become disposed above the mouth of the trachea;

(c) an inflatable-and-deflatable tubular balloon extending about and sealed to said distal end portion of said longer tube for sealingly engaging, in normal use, upon inflation thereof the wall of the esophagus below the mouth of the trachea and, upon abnormal use, for sealingly engaging the wall of the trachea; and (d) an inflatable-and-deflatable tubular balloon extending about and sealed to the distal end portion of said shorter tube for simultaneously sealing off, in normal use, upon inflation thereof, the air passageways leading to the nose and to the mouth of the patient, thereby allowing, in normal use, with said two balloons inflated, air to flow through said annular passageway into the patient's lungs.

2. The airway device of claim 1, and further including a suction tube removably extending through said longer tube and positioned for suctioning the stomach when said longer tube is in the esophagus while administering artificial respiration to the lungs through said annular passageway.

3. The airway device of claim 1, and further including a suction tube removably extending through said annular passageway and positioned for suctioning the stomach when said longer tube is in the trachea while administering artificial respiration to the lungs through said longer tube.

4. The airway device of claim 1, and further including a suctioning tube removably extending through said annular passageway and positioned for suctioning the lungs when said longer tube is in the esophagus while administering artificial respiration to the lungs through said annular passageway.

* * * * *